(12) United States Patent
Senetar et al.

(10) Patent No.: US 7,728,185 B2
(45) Date of Patent: Jun. 1, 2010

(54) INTEGRATION OF OLEFIN CRACKING WITH METATHESIS TO INCREASE LIGHT OLEFINS PRODUCTION

(75) Inventors: John J. Senetar, Naperville, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 561 days.

(21) Appl. No.: 11/781,505

(22) Filed: Jul. 23, 2007

(65) Prior Publication Data

US 2009/0030252 A1 Jan. 29, 2009

(51) Int. Cl.
- C07C 2/06 (2006.01)
- C07C 2/58 (2006.01)
- C07C 4/02 (2006.01)
- C07C 6/04 (2006.01)
- C07C 5/05 (2006.01)

(52) U.S. Cl. .................. 585/324; 585/329; 585/330; 585/331; 585/648; 585/643; 585/502; 585/709; 585/259

(58) Field of Classification Search .................. 585/329, 585/330, 331, 648, 643, 502, 709, 259
See application file for complete search history.

(56) References Cited

U.S. PATENT DOCUMENTS

| | | | |
|---|---|---|---|
| 5,026,936 A | 6/1991 | Leyshon et al. | 585/315 |
| 6,399,843 B1 | 6/2002 | Koves | 585/510 |
| 6,548,721 B1 | 4/2003 | McCulloch et al. | 585/277 |
| 6,586,649 B1 | 7/2003 | Botha et al. | 585/646 |
| 6,590,132 B1 | 7/2003 | Vora | 585/809 |
| 6,689,927 B1 | 2/2004 | Frame et al. | 585/510 |
| 6,875,900 B2 | 4/2005 | Koves | 585/510 |
| 6,916,448 B2 | 7/2005 | Commereuc et al. | |
| 2003/0176754 A1 | 9/2003 | Gartside et al. | |
| 2006/0089517 A1 | 4/2006 | Podrebarac et al. | |
| 2007/0135668 A1 | 6/2007 | Sumner | |

*Primary Examiner*—Thuan Dinh Dang
(74) *Attorney, Agent, or Firm*—Arthur E. Gooding

(57) ABSTRACT

A process for increasing the propylene yields for hydrocarbon cracking processes. The process includes adding using alkylation of the C4s coming from the hydrocarbon cracker, and passing larger olefins to an olefin cracking unit.

4 Claims, 1 Drawing Sheet

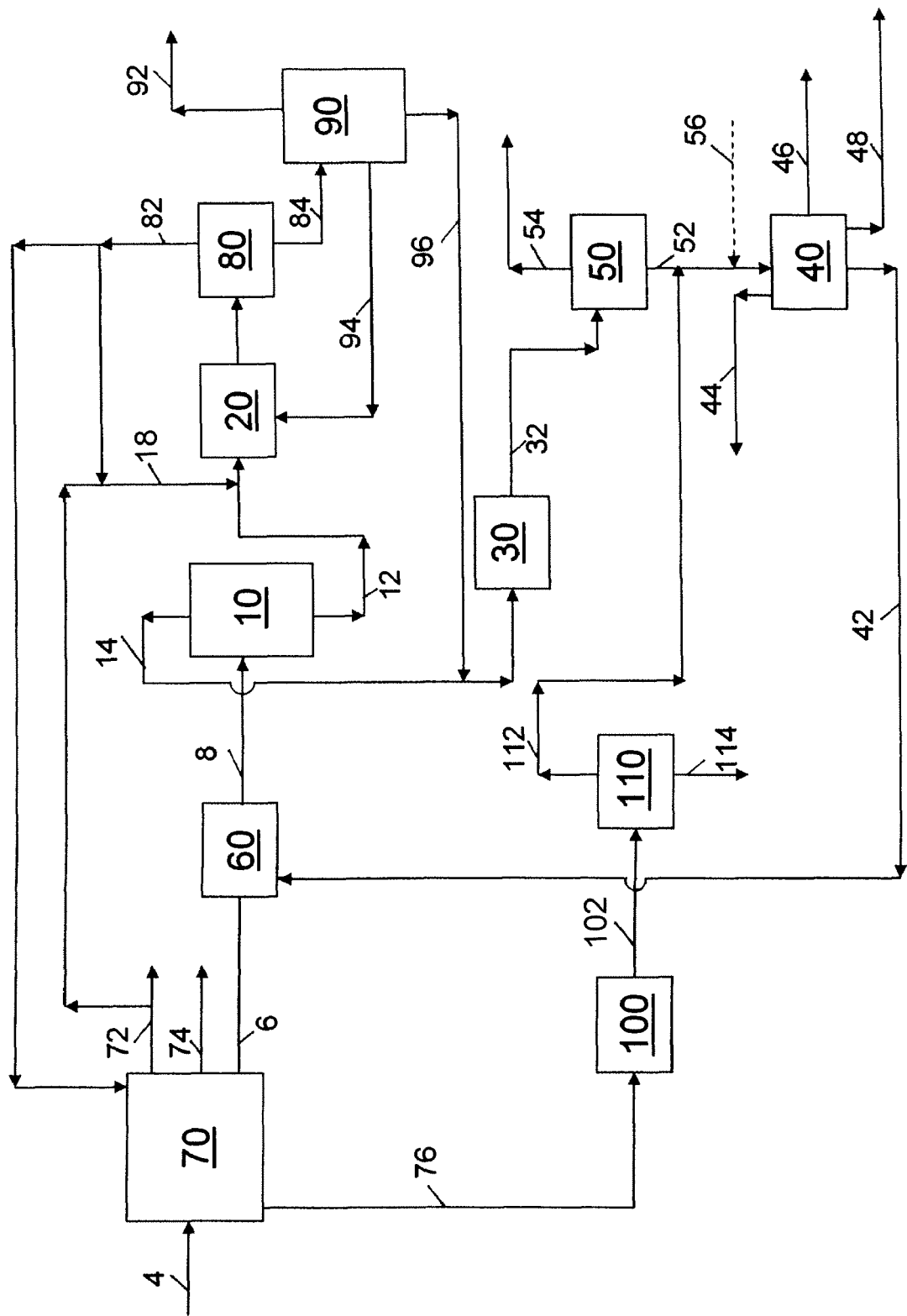

INTEGRATION OF OLEFIN CRACKING WITH METATHESIS TO INCREASE LIGHT OLEFINS PRODUCTION

FIELD OF THE INVENTION

This invention relates to the production of light olefins from the cracking of heavier olefins.

BACKGROUND OF THE INVENTION

Ethylene and propylene, light olefin hydrocarbons with two or three atoms per molecule, respectively, are important chemicals for use in the production of other useful materials, such as polyethylene and polypropylene. Polyethylene and polypropylene are two of the most common plastics found in use today and have a wide variety of uses for both as a material fabrication and as a material for packaging. Other uses for ethylene and propylene include the production of vinyl chloride, ethylene oxide, ethylbenzene and alcohol. Steam cracking or pyrolysis of hydrocarbons produces essentially all of the ethylene and propylene. While hydrocarbons used as feedstock for light olefin production include natural gas, petroleum liquids, and carbonaceous materials including coal, recycled plastics or any organic material, an important source is naphtha where larger paraffins and naphthenes are cracked to produce olefins.

One means of increasing propylene yields from a naphtha cracker is to add a metathesis reactor. A metathesis reactor can convert a portion of a feedstream comprising ethylene and butene to propylene. However, the metathesis reaction uses some of the ethylene which otherwise would be used as a product, and the butene stream needs to have isobutenes removed, as well as having 1-butene removed to improve the performance of the metathesis reactor.

As the demand for propylene increases, it is highly desirable to be able to shift production of propylene without having to create a new type of reactor, or to replace expensive existing equipment.

SUMMARY OF THE INVENTION

The present invention is a process for increasing the yields of propylene from a hydrocarbon cracking unit. The process comprises adding an alkylation reactor and an olefin cracking unit to convert a portion of effluent products from the hydrocarbon cracking unit that were not processed to ethylene or propylene. The process comprises separating a C4 stream into a normal butane stream comprising n-butane and 2-butene, and an isobutane stream comprising isobutane, isobutene and 1-butene. The isobutane stream is passed to an alkylation reactor to dimerize some of the isobutane stream to form larger hydrocarbons having 8 or more carbon atoms. The larger hydrocarbons are readily separated from unreacted C4s and are passed to an olefin cracking unit. The olefin cracking unit produces ethylene and propylene, and produces a stream rich in butanes and butenes for recycle to the metathesis reactor. Recycling and processing non-ethylene and non-propylene streams from the hydrocarbon cracking unit increases the yields of propylene by processing some of the streams through the alkylation reactor and olefin cracking unit.

In a variation on this invention, the process includes recovering pentenes from a pyrolysis gas, or pygas, generated by the hydrocarbon cracking unit. The pygas is selectively hydrogenated to remove diolefins, and the pentenes are separated and passed to an olefin cracking unit to produce additional ethylene and propylene.

Other objects, advantages and applications of the present invention will become apparent to those skilled in the art from the following drawing and detailed description.

BRIEF DESCRIPTION OF THE DRAWING

The FIGURE is a flow scheme for the increased production of propylene using the present invention.

DETAILED DESCRIPTION OF THE INVENTION

Propylene demands are growing and propylene is a more valuable light olefin than ethylene. The primary production of light olefins is through cracking, either steam or catalytic cracking, and produces a product mix of ethylene and propylene. Adjustments in operating conditions, and the types of catalysts used can influence the relative amounts of propylene and ethylene produced. It is desirable to increase the propylene yields because of the increased demand for propylene. Cracking also produces other products, and among them are a mixture of butanes and butenes. One method of increasing the propylene yields is to use a metathesis reactor to use the less valuable butanes and butenes to react with some of the ethylene to produce propylene.

In metathesis, ethylene reacts with 2-butent to form propylene. However, the increased propylene production is attained at the consumption of ethylene, and metathesis does not convert 1-butenes to propylene, but rather undesirable reactions occur between 1-butene and 2-butene that consume reactants without generating more propylene. The presence of isobutylene can also lead to oligomerization reactions and the accelerated deactivation of the metathesis catalyst. Removing 1-butenes can prevent the undesirable side reactions, but this does not increase the propylene production. However, rebuilding the cracked hydrocarbons, and then re-cracking the resulting compounds can be a productive method of increasing propylene yields with relatively small capital investments. This is not an obvious approach, because one is taking undesirable C4s, isobutane, isobutene, and 1-butene and building them up into larger hydrocarbons, C8+ and then breaking them back down to produce more n-butane and 2-butene, which are subsequently reacted with ethylene to create more propylene. The dimerization of unconverted C4s from metathesis permits the separation of saturated butanes from the dimerized butylenes. Recent experiments have demonstrated good conversion of di-isobutylene, the dimer of isobutene, in olefin cracking units. This presents a new approach for increasing propylene production from cracking units that generate a C4 stream.

The process for the present invention is shown in the FIGURE, where the light olefin production from naphtha is changed to increase the relative amounts of propylene, without having to drastically alter an existing light olefin production process. The naphtha is cracked and generates a C4 stream 6 which comprises butanes, butenes, isobutanes and isobutenes. The C4 stream is passed to a de-isobutanizer 10 where the C4 stream 8 is separated into a normal butane stream 12 comprising n-butane and 2-butene, and an isobutane stream 14 comprising isobutane, isobutene and 1-butene. The normal butane stream 12 is passed to a metathesis reactor 20, along with an ethylene stream 18, where the ethylene and normal butane stream react to form an effluent stream 22 rich in propylene. The isobutane stream 14 is passed to an alkylation reactor 30 where the isobutanes, isobutenes and 1-butenes are reacted to form an effluent stream 32 comprising hydrocarbons having 8 or more carbons atoms. The alkylation effluent stream 32 is passed to an olefin cracking unit 40 where the larger hydrocarbons are cracked into an effluent stream 42 comprising butanes and butenes. The olefin effluent stream 42 is passed to the de-isobutanizer 10 where the n-butanes and 2-butenes are recovered for use in the metathesis reactor 20.

An olefin cracking unit 40 converts larger olefins, C4s and larger, to light olefins of ethylene and propylene, but primarily propylene. The production of light olefins from the olefin cracking unit 40 does not consume ethylene, and the overall conversion of larger olefins to ethylene and propylene is about 60%, with a reasonable amount of recycle. The olefin cracker 40 also produces butenes when there are a significant amount of C5+ olefins. The butenes can be recycled for use in the metathesis reactor 20 or the alkylation reactor 30. The recycled butenes are reprocessed to increase the overall yields of light olefins.

In one embodiment, efficiency is improved by first passing the alkylation effluent stream 32 to a de-butanizer 50, separating the effluent stream 32 into an olefin cracking unit feedstream 52 rich in hydrocarbons having 8 or more carbon atoms, and a de-butanizer effluent stream 54 comprising butanes and butenes. The olefin cracking unit feedstream 52 is passed to the olefin cracking unit 40 for producing butanes and butenes and light olefins. The light olefins, ethylene and propylene, are separated and recovered in stream 44. The de-butanizer effluent stream 54 can be passed to a cracking furnace.

Feed pretreatment using selective hydrogenation and isomerization and increase the yields and overall efficiency of an olefin cracking process. In a preferred embodiment the process include the removal of diolefins from the C4 stream 6 before passing the C4 stream 6 to the de-isobutanizer 10. The C4 stream 6 is first passed to a selective hydrogenation reactor 60 to convert diolefins, and especially butadienes, to olefins, and to create a diolefin reduced C4 stream 8 which is passed to the de-isobutanizer 10. In addition the hydrogenation reactor 60 isomerizes 1-butene to 2-butene, which contributes to the production of propylene. Likewise, it is preferred to remove diolefins from the olefin cracking unit effluent stream 42, and therefore, the effluent stream 42 is passed first to the selective hydrogenation reactor 60 prior to passing to the de-isobutanizer 10.

In operation of this process, it is preferred to limit the alkylation of butenes to dimerization, and it is preferred that the alkylation reactor 30 is an oligomerization reactor, which will preferentially produce the dimer of butylene. Ethylene used in this process can come from any cracking unit that generates ethylene. In particular, a common unit is a naphtha cracking unit 70 which generates an ethylene stream 72, a propylene stream 74, a pygas stream 76, and a C4 stream 6 for use in the present invention. The naphtha cracking unit 70 receives a naphtha feedstream 4 comprising C5+ hydrocarbons. Another example of a cracking unit that can be adapted to include the present invention is a fluidized catalytic cracking (FCC) unit, which is used to generate ethylene and propylene, but also will generate heavier components, such as C4s. While the naphtha cracker is used in the example, any hydrocarbon cracking process used for the production of ethylene and propylene can be retrofitted with this invention to increase ethylene and propylene production.

The metathesis reactor 20 generates an effluent that comprises propylene, which is the desired product, but also includes ethylene and butanes and butenes. The effluent stream 22 is passed to a de-ethanizer 80 for removal of ethane and ethylene. The ethane and ethylene stream 82 can be recycled to the metathesis reactor 20 for further use as ethylene feedstock for conversion to propylene. The de-ethanizer 80 passes a second stream 84 comprising propylene and butanes and butenes to a de-propanizer 90 which generates a propylene product stream 92. In addition, the de-propanizer 90 generates a second stream 94 rich in n-butane and 2-butene which is passed as feed to the metathesis reactor 20 for conversion to propylene. A third stream 96 rich in isobutanes, isobutenes, and 1-butene is passed to the alkylation reactor 30 for the formation of di-isobutylene. While the current example shows one method of separating the product, propylene, and recovering ethylene and butanes and butenes, other sequences and separation processes for separating the propylene and recovering the ethylene and butanes and butenes are contemplated by this invention.

In one embodiment, invention is incorporated into a naphtha cracker for increased production of propylene. The process for producing ethylene and propylene is to pass a naphtha feedstock 4 and to crack the naphtha feedstock 4 in a cracking reactor 70. From the naphtha cracker 70 an effluent can be separated into an ethylene stream 72; a propylene stream 74; a C4 stream 6 comprising butanes, butenes, isobutanes, isobutenes, and butadienes; and a pyrolysis gas stream 76, also known as a pygas stream. The effluent streams are separated and the C4 stream is passed to a selective hydrogenation reactor 60 to reduce the diolefin content. The effluent stream from the hydrogenation reactor 60 is then passed to a de-isobutanizer 10 to separate the isobutanes, isobutenes and 1-butenes from the C4 stream, and generate a normal butane stream 12, comprising n-butane and 2-butene, and an isobutane stream 14 comprising isobutane, isobutene, and 1-butene. The normal butane stream 12 is passed to a metathesis reactor 20, along with a portion of the ethylene stream 72 from the naphtha cracker 70 for conversion to propylene.

Recovering the isobutane stream 14 and passing the isobutane stream 14 to an alkylation reactor 30 produces and effluent stream 32 comprising larger hydrocarbons having 8 or more carbon atoms, and depleted in isobutane and butenes. The effluent stream 32 is separated in a de-butanizer 50 to generate a hydrocarbon stream 52 comprising hydrocarbons having 8 or more carbon atoms. The alkylation reactor 30 is effective in generating di-isobutylene which is readily separated from much lighter C4s. The hydrocarbon stream 52 is passed to an olefin cracking unit 40 to increase the light olefin yields, of ethylene and propylene 44. C4s produced in the olefin cracking unit 40 are recycled in the process to the selective hydrogenation reactor 60 to convert diolefins to olefins.

In a variation of this embodiment, the metathesis reactor 20 generates an unconverted butane stream 96 comprising butanes and butenes. The unconverted butane stream 96 is passed to the alkylation reactor 30 for recycling of hydrocarbons not converted into ethylene or propylene 44. In the present invention, it is preferred that the alkylation reactor 30 is an oligomerization reactor.

In another embodiment, the pygas contains useful components that can be processed to produce light olefins. The pygas stream 76 can be selectively hydrogenated in a selective hydrogenation reactor 100 primarily to remove diolefins, and the effluent stream 102 enriched in olefins. The effluent stream 102 can be separated into a C5 stream 112 comprising pentenes and pentanes and a heavy aromatic stream 114 for further processing. The C5 stream 112 is passed to the olefin cracking unit 40 for the production of ethylene and propylene.

Unreacted butanes can be recycled back to cracker furnaces for further cracking.

The integration of other units with the naphtha cracker was modeled to demonstrate the increase in propylene yields. The comparison uses the same feed and process conditions for the naphtha cracker. The processes add units that affect the relative amounts of ethylene and propylene, as well as the overall production of ethylene and propylene. The naphtha cracker is operated at a severity of 0.68 and the product flow rates are in tons/hour (t/h). The models show the increases in yields by diverting non-light olefin streams to the additional units. The use of alkylation with the olefin cracking (OC) shows a significant increase in yield for the same feed. The addition of the alkylation reactor and olefin cracking unit increase the yield of propylene substantially beyond that of just adding the metathesis reactor. In addition, with the addition of the olefin cracking unit, additional propylene can be produced from the pygas that is a natural effluent stream from the naphtha cracker. The model assumes a modeling feed of 250.4 tons/hr of naphtha feed to the naphtha cracker. The additional FCC feed assumes an additional feed of 39.2 tons/hr of a hydrocarbon stream comprising C5 to C7 hydrocarbons fed to an FCC unit and cracked to produce additional light olefins, and where the FCC generates an additional feed to the OC unit.

TABLE 1

Modeling Results

|  | Ethylene | Propylene |
|---|---|---|
| Base case-stand alone cracker | 71.4 | 43.4 |
| Cracker and metathesis | 63.2 | 67.9 |
| Contribution from metathesis | −8.2 | 24.5 |
| Cracker, metathesis and OC | 64.2 | 78.5 |
| Contribution from metathesis | −9.3 | 28 |
| Contribution from OC | 2.1 | 7.1 |
| Additional yields over base case | −7.2 | 35.1 |
| Cracker, metathesis, and OC with additional FCC feed | 65.2 | 90.5 |
| Contribution from metathesis | −10.7 | 32 |
| Contribution from OC | 4.5 | 15.1 |
| Additional yields over base case | −6.2 | 47.1 |

The increase in production of propylene through the use of an alkylation reactor with an olefin cracking unit can be accomplished without decreasing the ethylene production over a reactor and metathesis operation. The simulation also shows that recombining C4 and C5 olefins to larger olefins is a useful and economic method of increasing propylene yields from naphtha feedstocks.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for increasing the yield of propylene from hydrocarbons comprising:
    passing a hydrocarbon feedstream to a cracking unit, thereby creating an effluent;
    separating the effluent into an ethylene stream, a propylene stream, a C4 stream, and a pygas stream;
    passing the C4 stream to a selective hydrogenation reactor thereby creating a C4 effluent stream having a reduced diolefin content;
    separating the C4 effluent stream into a normal butane stream comprising n-butane and 2-butene, and isobutane stream comprising isobutane, isobutene and 1-butene;
    passing the normal butane stream and the ethylene stream to a metathesis reactor, thereby creating a propylene stream;
    passing the isobutane stream to an alkylation and oligomerization reactor, thereby creating an alkylation effluent stream comprising hydrocarbons having 8 or more carbon atoms, and depleted in butanes and butenes;
    separating the alkylation effluent stream into an olefin cracking unit feedstream rich in hydrocarbons having 8 or more carbon atoms, and a butane effluent stream having butanes and butenes;
    passing the olefin cracking unit feedstream to an olefin cracking unit, thereby creating a second C4 stream, comprising butanes and butenes, and a second effluent stream rich in ethylene and propylene; and
    passing the second C4 stream to the selective hydrogenation reactor.

2. The process of claim 1 wherein the metathesis reactor also generates an unconverted butane stream comprising butanes and butenes, and the unconverted butane stream is passed to the alkylation and oligomerization reactor.

3. The process of claim 1 further comprising:
    passing the pygas stream to a selective hydrogenation reactor, thereby generating a pygas effluent stream enriched in olefins;
    separating the pygas effluent stream into an olefin stream comprising C5 olefins and C5 paraffins, and a heavy aromatics stream; and
    passing the olefin stream to the olefin cracking unit.

4. The process of claim 1 wherein the selective hydrogenation reactor also isomerizes the butanes.

* * * * *

UNITED STATES PATENT AND TRADEMARK OFFICE
CERTIFICATE OF CORRECTION

| | | |
|---|---|---|
| PATENT NO. | : 7,728,185 B2 | Page 1 of 1 |
| APPLICATION NO. | : 11/781505 | |
| DATED | : June 1, 2010 | |
| INVENTOR(S) | : Senetar et al. | |

It is certified that error appears in the above-identified patent and that said Letters Patent is hereby corrected as shown below:

Column 6,
Claim 2,
Line 37, replace "passed to the alkylation and oligomerization reactor" with --passed to the alkylation or oligomerization reactor--.

Signed and Sealed this
Twenty-eighth Day of December, 2010

David J. Kappos
*Director of the United States Patent and Trademark Office*